(12) United States Patent
Saygili

(10) Patent No.: US 11,154,670 B2
(45) Date of Patent: Oct. 26, 2021

(54) CARTRIDGE ASSEMBLY HAVING AN ACTUATION PORTION

(71) Applicant: Philip Morris Products S.A., Neuchatel (CH)

(72) Inventor: Ali Murat Saygili, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 314 days.

(21) Appl. No.: 16/069,650

(22) PCT Filed: Jan. 25, 2017

(86) PCT No.: PCT/EP2017/051545
§ 371 (c)(1),
(2) Date: Jul. 12, 2018

(87) PCT Pub. No.: WO2017/129615
PCT Pub. Date: Aug. 3, 2017

(65) Prior Publication Data
US 2019/0029320 A1 Jan. 31, 2019

(30) Foreign Application Priority Data
Jan. 25, 2016 (EP) ..................................... 16152628

(51) Int. Cl.
*A61M 15/06* (2006.01)
*A61M 11/00* (2006.01)
(Continued)

(52) U.S. Cl.
CPC ............. *A61M 15/06* (2013.01); *A24F 40/30* (2020.01); *A24F 40/42* (2020.01); *A24F 40/485* (2020.01);
(Continued)

(58) Field of Classification Search
None
See application file for complete search history.

(56) References Cited

U.S. PATENT DOCUMENTS

| 2014/0182608 A1 | 7/2014 | Egoyants et al. |
| 2015/0258289 A1 | 9/2015 | Henry, Jr. et al. |

(Continued)

FOREIGN PATENT DOCUMENTS

| CN | 104906669 A | 9/2015 |
| CN | 105153610 A | 12/2015 |

(Continued)

OTHER PUBLICATIONS

Combined Russian Federation Office Action and Search Report dated Jun. 5, 2020 in Russian Federation Patent Application No. 2018130655/14(049853) (with English translation), citing documents AO and AP therein, 22 pages.

(Continued)

*Primary Examiner* — Phu H Nguyen
(74) *Attorney, Agent, or Firm* — Oblon, McClelland, Maier & Neustadt, L.L.P.

(57) ABSTRACT

A cartridge assembly for an aerosol-generating system is provided, including a cartridge and a mouthpiece. The cartridge includes a cartridge body and a cartridge cover, the body having a first side defining a first recess and a second side defining a second recess. The cover includes a cartridge cover cavity in which the cartridge body is slidably received and an actuation aperture configured to receive an actuation portion of an aerosol-generating device. The cartridge assembly is configured so that, when an actuation portion of an aerosol-generating device is received against the cartridge body through the actuation aperture, the cartridge body is slidable within the cartridge cover cavity from a first position to a second position. In the first position, airflow through the first and second recesses is prevented. In the (Continued)

second position, airflow through the first and second recesses is enabled.

15 Claims, 2 Drawing Sheets

(51) Int. Cl.
  *A24F 40/30* (2020.01)
  *A24F 40/42* (2020.01)
  *A24F 40/485* (2020.01)
  *A24F 40/20* (2020.01)
  *A24F 40/46* (2020.01)
  *A24F 40/465* (2020.01)

(52) U.S. Cl.
  CPC .............. *A61M 11/00* (2013.01); *A24F 40/20* (2020.01); *A24F 40/46* (2020.01); *A24F 40/465* (2020.01)

(56) References Cited

U.S. PATENT DOCUMENTS

| | | |
|---|---|---|
| 2016/0022930 A1 | 1/2016 | Greim et al. |
| 2016/0143356 A1 | 5/2016 | Poget et al. |
| 2016/0286862 A1 | 10/2016 | Silvetrini |

FOREIGN PATENT DOCUMENTS

| | | |
|---|---|---|
| EP | 2 653 182 A1 | 10/2013 |
| EP | 2 753 201 B1 | 2/2016 |
| WO | WO 2008/121610 A1 | 10/2008 |
| WO | WO 2013/083635 A1 | 6/2013 |
| WO | WO 2014/140320 A1 | 9/2014 |
| WO | WO 2015/000974 A1 | 1/2015 |
| WO | WO 2015/022317 A1 | 2/2015 |
| WO | WO 2015/082651 A1 | 6/2015 |
| WO | WO 2015/105895 A1 | 7/2015 |
| WO | WO 2015/197627 A1 | 12/2015 |
| WO | WO 2017/032695 A1 | 3/2017 |
| WO | WO 2017/108983 A1 | 6/2017 |

OTHER PUBLICATIONS

Combined Chinese Office Action and Search Report dated Dec. 21, 2020 in corresponding Chinese Patent Application No. 201780005523.7 (with English Translation) citing documents AA and AO-AT therein, 8 pages.

International Search Report dated Mar. 7, 2017 in PCT/EP2017/051545 filed Jan. 25, 2017.

Combined Chinese Office Action and Search Report dated Jul. 16, 2020 in corresponding Chinese Patent Application No. 201780005523.7 (with English Translation) citing documents AO-AR therein, 19 pages.

Extended European Search Report dated Apr. 1, 2016 in Patent Application No. 16152628.0.

CARTRIDGE ASSEMBLY HAVING AN ACTUATION PORTION

The present invention relates to a cartridge assembly for use in an aerosol-generating system and an aerosol-generating system comprising the cartridge assembly. The present invention finds particular application as a cartridge assembly comprising a nicotine source and an acid source for the generation of an aerosol comprising nicotine salt particles.

Devices for delivering nicotine to a user and comprising a nicotine source and a volatile delivery enhancing compound source are known. For example, WO 2008/121610 A1 discloses devices in which nicotine and a volatile acid, such as pyruvic acid, are reacted with one another in the gas phase to form an aerosol of nicotine salt particles that is inhaled by the user.

In WO 2008/121610 A1 the nicotine source and volatile delivery enhancing compound source may be housed in compartments that are sealed by one or more removable or frangible barriers prior to initial use of the aerosol-generating system.

However, the inclusion of one or more removable or frangible barriers may disadvantageously increase the cost and complexity of manufacturing such aerosol-generating systems. Consequently, it would be desirable to provide a cartridge assembly for use in an aerosol-generating system in which one or more volatile compounds may be retained during storage without the use of removable or frangible barriers.

According to a first aspect of the present invention there is provided a cartridge assembly for use in an aerosol-generating system, the cartridge assembly comprising a cartridge and a mouthpiece. The cartridge comprises a cartridge body and a cartridge cover, the cartridge body having a first side defining a first recess and a second side defining a second recess. The cartridge cover comprises a cartridge cover cavity in which the cartridge body is slidably received and a cartridge cover opening at a downstream end of the cartridge cover cavity. The cartridge cover further comprises a cartridge cover wall portion extending across an upstream end of the cartridge cover cavity and comprising a cartridge cover air inlet, and an actuation aperture in the cartridge cover wall portion for receiving an actuation portion of an aerosol-generating device. The mouthpiece comprises a mouthpiece cavity in which a downstream end of the cartridge is received. The cartridge is configured so that, when an actuation portion of an aerosol-generating device is received against the cartridge body through the actuation aperture, the cartridge body slides within the cartridge cover cavity from a first position to a second position. In the first position, an upstream end of the cartridge body abuts the cartridge cover wall portion and obstructs the cartridge cover air inlet, and a downstream end of the cartridge body abuts a downstream end of the cartridge cover and obstructs the cartridge cover opening. In the second position, the upstream end of the cartridge body is spaced apart from the cartridge cover wall portion and the downstream end of the cartridge body is spaced apart from the downstream end of the cartridge cover so that the cartridge cover air inlet is in fluid communication with the cartridge cover opening via the first recess and the second recess.

As used herein with reference to the invention, the term "air inlet" is used to describe one or more apertures through which air may be drawn into a component or portion of a component of the cartridge assembly.

As used herein with reference to the invention, the term "air outlet" is used to describe one or more apertures through which air may be drawn out of a component or portion of a component of the cartridge assembly.

As used herein with reference to the invention, by "obstructed" it is meant that an air inlet or an air outlet is blocked such that airflow through the air inlet or the air outlet is substantially prevented.

Advantageously, a cartridge assembly according to the present invention minimises or substantially prevents the loss of one or more volatile compounds stored within the cartridge before the cartridge assembly is used in an aerosol-generating system. Specifically, the obstruction of the cartridge cover air inlet and the cartridge cover opening by the cartridge body when the cartridge body is in the first position may minimise or substantially prevent the loss of one or more volatile compounds stored within the cartridge.

Advantageously, by using the cartridge body to obstruct the cartridge cover air inlet and the cartridge cover opening, the cartridge body being slidable with respect to the cartridge cover, a cartridge assembly according to the present invention can eliminate the need to use one or more removable or frangible barriers to seal the cartridge.

Advantageously, a cartridge assembly according to the present invention provides a reliable and consistent means for activating the cartridge assembly. Specifically, the cartridge assembly being configured so that the cartridge body moves from the first position to the second position when an actuation portion of an aerosol-generating device is received against the cartridge body through the actuation aperture may provide automatic activation of the cartridge assembly when the cartridge assembly is combined with an aerosol-generating device to form an aerosol-generating system.

The actuation aperture may comprise a single actuation aperture. The actuation aperture may comprise a plurality of actuation apertures, each actuation aperture configured to receive an actuation portion of an aerosol-generating device.

The cartridge cover air inlet may comprise one or more inlet apertures. The actuation aperture may be separate from one or more inlet apertures forming the cartridge cover air inlet.

An inlet aperture forming at least part of the cartridge cover air inlet may form the actuation aperture. In embodiments in which the cartridge cover air inlet comprises a single inlet aperture, the single inlet aperture may form the actuation aperture. In embodiments in which the cartridge cover air inlet comprises a plurality of inlet apertures, at least one of the inlet apertures may form the actuation aperture. A plurality of inlet apertures forming at least part of the cartridge cover air inlet may also form a plurality of actuation apertures. Each inlet aperture forming the cartridge cover air inlet may also form an actuation aperture. Advantageously, using one or more inlet apertures to form one or more actuation apertures may simplify the construction of the cartridge cover by minimising the number of apertures formed in the cartridge cover wall portion.

When the cartridge body is in the second position, a first air inlet may provide fluid communication between the cartridge cover air inlet and the first recess. The first air inlet may comprise one or more apertures in an upstream portion of the cartridge body. The first air inlet may be defined between a portion of the cartridge body and a portion of the cartridge cover at an upstream end of the first recess. That is, the first air inlet may be defined by a gap between an upstream portion of the cartridge body and a portion of the cartridge cover when the cartridge body is in the second position.

When the cartridge body is in the second position, a second air inlet may provide fluid communication between the cartridge cover air inlet and the second recess. The second air inlet may comprise one or more apertures in an upstream portion of the cartridge body. The second air inlet may be defined between a portion of the cartridge body and a portion of the cartridge cover at an upstream end of the second recess. That is, the second air inlet may be defined by a gap between an upstream portion of the cartridge body and a portion of the cartridge cover when the cartridge body is in the second position.

When the cartridge body is in the second position, a first air outlet may provide fluid communication between the first recess and the cartridge cover opening. The first air outlet may comprise one or more apertures in a downstream portion of the cartridge body. The first air outlet may be defined between a portion of the cartridge body and a portion of the cartridge cover at a downstream end of the first recess. That is, the first air outlet may be defined by a gap between a downstream portion of the cartridge body and a portion of the cartridge cover when the cartridge body is in the second position.

When the cartridge body is in the second position, a second air outlet may provide fluid communication between the second recess and the cartridge cover opening. The second air outlet may comprise one or more apertures in a downstream portion of the cartridge body. The second air outlet may be defined between a portion of the cartridge body and a portion of the cartridge cover at a downstream end of the second recess. That is, the second air outlet may be defined by a gap between a downstream portion of the cartridge body and a portion of the cartridge cover when the cartridge body is in the second position.

The mouthpiece may comprise a mouthpiece wall portion extending across the downstream end of the mouthpiece cavity. A downstream end of the cartridge body may abut the mouthpiece wall portion when the cartridge body is in the second position. Advantageously, when the cartridge body is moving into the second position from the first position, the mouthpiece wall portion may prevent further movement of the cartridge body so that it does not move beyond the second position. Preventing movement of the cartridge body beyond the second position may ensure that a proper and desired airflow is obtained through the first recess and the second recess of the cartridge body when the cartridge assembly is used in an aerosol-generating system.

As described herein, the cartridge assembly may comprise a first air inlet, a second air inlet, a first air outlet and a second air outlet, each defined between a portion of the cartridge cover and a portion of the cartridge body. In such embodiments, providing a mouthpiece wall portion to prevent movement of the cartridge body beyond the second position may ensure that a desired flow area for each of the first and second air inlets and first and second air outlets is provided when the cartridge assembly is activated.

In embodiments in which the mouthpiece comprises a mouthpiece wall portion, the mouthpiece preferably comprises an airflow opening in the mouthpiece wall portion and in fluid communication with the cartridge cover opening when the cartridge body is in the second position. The airflow opening in the mouthpiece wall portion may be a mouthpiece air outlet providing fluid communication between the cartridge cover opening, when the cartridge body is in the second position, and the exterior of the mouthpiece.

The mouthpiece may comprise a mouthpiece chamber positioned downstream of the cartridge, wherein the mouthpiece further comprises a mouthpiece air outlet at a downstream end of the mouthpiece chamber. In embodiments in which the mouthpiece comprises a mouthpiece wall portion, the mouthpiece chamber is preferably positioned downstream of the mouthpiece wall portion. In embodiments in which the mouthpiece wall portion comprises an airflow opening, the airflow opening may be a mouthpiece air inlet providing fluid communication between the cartridge cover opening, when the cartridge body is in the second position, and the mouthpiece chamber.

Providing a mouthpiece chamber may be advantageous in embodiments in which a plurality of volatile reactants are stored separately within the cartridge assembly. That is, the volatile reactants may be reacted in the gas phase within the mouthpiece chamber before the reaction product is delivered to a user through the mouthpiece air outlet.

The mouthpiece may comprise a ventilation air inlet providing fluid communication between the exterior of the mouthpiece and the mouthpiece chamber, wherein the ventilation air inlet is position between the cartridge and the downstream end of the mouthpiece chamber. In embodiments in which the mouthpiece comprises a mouthpiece wall portion, preferably the ventilation air inlet is positioned between the mouthpiece wall portion and the downstream end of the mouthpiece chamber.

In any of the embodiments described herein, the cartridge assembly may further comprise a nicotine source positioned within the first recess and an acid source positioned within the second recess.

As used herein with reference to the invention, the term "nicotine", is used to describe nicotine, nicotine base or a nicotine salt.

The nicotine source may comprise a first carrier material impregnated with between about 1 milligram and about 50 milligrams of nicotine. The nicotine source may comprise a first carrier material impregnated with between about 1 milligram and about 40 milligrams of nicotine. Preferably, the nicotine source comprises a first carrier material impregnated with between about 3 milligrams and about 30 milligrams of nicotine. More preferably, the nicotine source comprises a first carrier material impregnated with between about 6 milligrams and about 20 milligrams of nicotine. Most preferably, the nicotine source comprises a first carrier material impregnated with between about 8 milligrams and about 18 milligrams of nicotine.

In embodiments in which the first carrier material is impregnated with nicotine base or a nicotine salt, the amounts of nicotine recited herein are the amount of nicotine base or amount of ionised nicotine, respectively.

The first carrier material may be impregnated with liquid nicotine or a solution of nicotine in an aqueous or non-aqueous solvent.

The first carrier material may be impregnated with natural nicotine or synthetic nicotine.

The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

Advantageously, the acid source comprises a second carrier material impregnated with acid.

The first carrier material and the second carrier material may be the same or different.

Advantageously, the first carrier material and the second carrier material have a density of between about 0.1 grams/cubic centimetre and about 0.3 grams/cubic centimetre.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug.

Advantageously, the shape and size of the first carrier material is similar to the shape and size of the first recess of the cartridge body.

The shape, size, density and porosity of the first carrier material may be chosen to allow the first carrier material to be impregnated with a desired amount of nicotine.

Advantageously, the first recess of the cartridge body may further comprise a flavourant. Suitable flavourants include, but are not limited to, menthol.

Advantageously, the first carrier material may be impregnated with between about 3 milligrams and about 12 milligrams of flavourant.

The second carrier material acts as a reservoir for the acid.

Advantageously, the second carrier material is chemically inert with respect to the acid.

The second carrier material may have any suitable shape and size. For example, the second carrier material may be in the form of a sheet or plug.

Advantageously, the shape and size of the second carrier material is similar to the shape and size of the second recess of the cartridge body.

The shape, size, density and porosity of the second carrier material may be chosen to allow the second carrier material to be impregnated with a desired amount of acid.

Advantageously, acid source is a lactic acid source comprising a second carrier material impregnated with between about 2 milligrams and about 60 milligrams of lactic acid.

Preferably, the lactic acid source comprises a second carrier material impregnated with between about 5 milligrams and about 50 milligrams of lactic acid. More preferably, the lactic acid source comprises a second carrier material impregnated with between about 8 milligrams and about 40 milligrams of lactic acid. Most preferably, the lactic acid source comprises a second carrier material impregnated with between about 10 milligrams and about 30 milligrams of lactic acid.

The shape and dimensions of the first recess of the cartridge body may be chosen to allow a desired amount of nicotine to be housed in the cartridge body.

The shape and dimensions of the second recess of the cartridge body may be chosen to allow a desired amount of acid to be housed in the cartridge body.

When the cartridge body is received within the cartridge cover, the first recess and an overlying portion of the cartridge cover may define a first compartment in which the nicotine source is positioned. When the cartridge body is received within the cartridge cover, the second recess and an overlying portion of the cartridge cover may define a second compartment in which the acid source is positioned. The ratio of nicotine and acid required to achieve an appropriate reaction stoichiometry may be controlled and balanced through variation of the volume of the first compartment relative to the volume of the second compartment.

In embodiments in which the cartridge assembly comprises a first air inlet, a second air inlet, a first air outlet and a second air outlet, the first air inlet of the first recess of the cartridge body and the second air inlet of the second recess of the cartridge body may each comprise one or more apertures. For example, the first air inlet of the first recess of the cartridge body and the second air inlet of the second recess of the cartridge body may each comprise one, two, three, four, five, six or seven apertures.

The first air inlet of the first recess of the cartridge body and the second air inlet of the second recess of the cartridge body may comprise the same or different numbers of apertures.

Advantageously, the first air inlet of the first recess of the cartridge body and the second air inlet of the second recess of the cartridge body each comprise a plurality of apertures. For example, the first air inlet of the first recess of the cartridge body and the second air inlet of the second recess of the cartridge body may each comprise two, three, four, five, six or seven apertures.

Providing a first air inlet comprising a plurality of apertures and a second air inlet comprising a plurality of apertures may advantageously result in more homogeneous airflow within the first recess and the second recess, respectively. In use, this may improve entrainment of nicotine in an air stream drawn through the first recess and improve entrainment of acid in an air stream drawn through the second recess.

The ratio of nicotine and acid required to achieve an appropriate reaction stoichiometry may be controlled and balanced through variation of the volumetric airflow through the first recess of the cartridge body relative to the volumetric airflow through the second recess of the cartridge body. The ratio of the volumetric airflow through the first recess relative to the volumetric airflow through the second recess may be controlled through variation of one or more of the number, dimensions and location of the apertures forming the first air inlet of the first recess of the cartridge body relative to the number, dimensions and location of the apertures forming the second air inlet of the second recess of the cartridge body.

In embodiments in which the acid source comprises lactic acid, advantageously the flow area of the second air inlet of the second recess of the cartridge body is greater than the flow area of the first air inlet of the first recess of the cartridge body.

As used herein with reference to the invention, the term "flow area" is used to describe the cross-sectional area of an air inlet or air outlet through which air flows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

Increasing the flow area of the second air inlet of the second recess of the cartridge body relative to the flow area of the first air inlet of the first recess of the cartridge body advantageously increases the volumetric airflow through the second air inlet compared to the volumetric airflow through the first air inlet.

In embodiments in which the acid source comprises lactic acid, preferably the ratio of the flow area of the first air inlet of the first recess of the cartridge body to the flow area of the second air inlet of the second recess of the cartridge body is between about 3:4 and about 1:2. More preferably, the ratio of the flow area of the first air inlet of the first recess of the cartridge body to the flow area of the second air inlet of the second recess of the cartridge body is between about 2:3 and about 1:2.

The flow area of the second air inlet of the second recess of the cartridge body may be increased relative to the flow area of the first air inlet of the first recess of the cartridge body by one or both of increasing the size of the one or more apertures forming the second air inlet relative to the size of the one or more apertures forming the first air inlet and increasing the number of apertures forming the second air inlet relative to the number of apertures forming the first air inlet.

Advantageously, the flow area of the second air inlet of the second recess of the cartridge body is increased relative to the flow area of the first air inlet of the first recess of the cartridge body by increasing the number of apertures forming the second air inlet relative to the number of apertures forming the first air inlet.

Advantageously, the first air inlet of the first recess of the cartridge body comprises between 2 and 5 apertures.

Advantageously, the second air inlet of the second recess of the cartridge body comprises between 3 and 7 apertures.

Advantageously, the flow area of the first air inlet of the first recess of the cartridge body is between about 0.1 square millimetres and about 1.6 square millimetres, more advantageously between about 0.2 square millimetres and about 0.8 square millimetres.

In embodiments in which the first air inlet of the first recess of the cartridge body comprises a plurality of apertures, the apertures may have different flow areas so that the flow area of the first air inlet of the first recess of the cartridge body is divided unequally between the apertures forming the first air inlet.

In embodiments in which the first air inlet of the first recess of the cartridge body comprises a plurality of apertures, each of the apertures may have the same flow area so that the flow area of the first air inlet of the first recess of the cartridge body is divided equally between the apertures forming the first air inlet. Providing a first air inlet comprising a plurality of apertures having substantially the same flow area may advantageously simplify manufacturing of the cartridge body.

The first air inlet of the first recess of the cartridge body may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

In embodiments in which the acid source comprises lactic acid, advantageously the flow area of the second air inlet of the second recess of the cartridge body is between about 0.2 square millimetres and about 2.4 square millimetres, more advantageously between about 0.4 square millimetres and about 1.2 square millimetres.

In embodiments in which the second air inlet of the second recess of the cartridge body comprises a plurality of apertures, the apertures may have different flow areas so that the total flow area of the second air inlet of the second recess of the cartridge body is divided unequally between the apertures forming the second air inlet.

In embodiments in which the second air inlet of the second recess of the cartridge body comprises a plurality of apertures, each of the apertures may have the same flow area so that the total flow area of the second air inlet of the second recess of the cartridge body is divided equally between the apertures forming the second air inlet. Providing a second air inlet comprising a plurality of apertures having substantially the same flow area may advantageously simplify manufacturing of the cartridge body.

The second air inlet of the second recess of the cartridge body may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

The first air outlet of the first recess of the cartridge body and the second air outlet of the second recess of the cartridge body may each comprise one or more apertures. For example, the first air outlet of the first recess of the cartridge body and the second air outlet of the second recess of the cartridge body may each comprise one, two, three, four, five, six or seven apertures.

The first air outlet of the first recess of the cartridge body and the second air outlet of the second recess of the cartridge body may comprise the same or different numbers of apertures.

Advantageously, the first air outlet of the first recess of the cartridge body and the second air outlet of the second recess of the cartridge body may each comprise a plurality of apertures. For example, the first air outlet of the first recess of the cartridge body and the second air outlet of the second recess of the cartridge body may each comprise two, three, four, five, six or seven apertures. Providing a first air outlet comprising a plurality of apertures and a second air outlet comprising a plurality of apertures may advantageously result in more homogeneous airflow within the first recess and the second recess, respectively. In use, this may improve entrainment of nicotine in an air stream drawn through the first recess and improve entrainment of acid in an air stream drawn through the second recess.

In embodiments in which the first air outlet of the first recess of the cartridge body comprises a plurality of apertures, advantageously the first air outlet comprises between 2 and 5 apertures.

In embodiments in which the second air outlet of the second recess of the cartridge body comprises a plurality of apertures, advantageously, the second air outlet comprises between 3 and 7 apertures.

Advantageously, the first air outlet of the first recess of the cartridge body and the second air outlet of the second recess of the cartridge body may each comprise a single aperture. Providing a first air outlet comprising a single aperture and a second recess having a second air outlet comprising a single aperture may advantageously simplify manufacturing of the cartridge body.

The ratio of nicotine and acid required to achieve an appropriate reaction stoichiometry may be controlled and balanced through variation of the volumetric airflow through the first recess of the cartridge body relative to the volumetric airflow through the second recess of the cartridge body. The ratio of the volumetric airflow through the first recess relative to the volumetric airflow through the second recess may be controlled through variation of one or more of the number, dimensions and location of the apertures forming the first air outlet of the first recess of the cartridge body relative to the number, dimensions and location of the apertures forming the second air outlet of the second recess of the cartridge body.

The flow area of the first air outlet of the first recess may be the same as or different to the flow area of the second air outlet of the second recess.

The flow area of the second air outlet of the second recess of the cartridge body may be greater than flow area of the first air outlet of the first recess of the cartridge body.

Increasing the flow area of the second air outlet of the second recess of the cartridge body relative to the flow area of the first air outlet of the first recess of the cartridge body may advantageously increase the volumetric airflow through the second air outlet compared to the volumetric airflow through the first air outlet.

In embodiments in which the acid source comprises lactic acid, the ratio of the flow area of the first air outlet of the first recess of the cartridge body to the flow area of the second air outlet of the second recess of the cartridge body is preferably between about 3:4 and about 1:2. More preferably, the ratio of the flow area of the first air outlet of the first recess of the cartridge body to the flow area of the second air outlet of the second recess of the cartridge body is between about 2:3 and about 1:2.

In embodiments in which the flow area of the second air outlet of the second recess of the cartridge body is greater than flow area of the first air outlet of the first recess of the cartridge body, the flow area of the second air outlet of the second recess of the cartridge body may be increased relative to the flow area of the first air outlet of the first recess of the cartridge body by one or both of increasing the size of the one or more apertures forming the second air outlet relative to the size of the one or more apertures forming the first air outlet and increasing the number of apertures forming the second air outlet relative to the number of apertures forming the first air outlet.

Advantageously, the flow area of the second air outlet of the second recess of the cartridge body is increased relative to the flow area of the first air outlet of the first recess of the cartridge body by increasing the number of apertures forming the second air outlet relative to the number of apertures forming the first air outlet.

The first air inlet and the first air outlet of the first recess of the cartridge body may comprise the same or different numbers of apertures.

Advantageously, the first air inlet and the first air outlet of the first recess of the cartridge body comprise the same numbers of apertures. Providing a first air inlet and a first air outlet comprising the same number of apertures may advantageously simplify manufacturing of the cartridge body.

The second air inlet and the second air outlet of the second recess of the cartridge body may comprise the same or different numbers of apertures.

Advantageously, the second air inlet and the second air outlet of the second recess of the cartridge body comprise the same numbers of apertures. Providing a second air inlet and a second air outlet comprising the same number of apertures may advantageously simplify manufacturing of the cartridge body.

Advantageously, the flow area of the first air outlet of the first recess of the cartridge body is between about 0.1 square millimetres and about 5 square millimetres.

In embodiments in which the first air outlet of the first recess of the cartridge body comprises a plurality of apertures, the apertures may have different flow areas so that the flow area of the first air outlet of the first recess of the cartridge body is divided unequally between the apertures forming the first air outlet.

In embodiments in which the first air outlet of the first recess of the cartridge body comprises a plurality of apertures, each of the apertures may have the same flow area so that the flow area of the first air outlet of the first recess of the cartridge body is divided equally between the apertures forming the first air outlet. Providing a first air outlet comprising a plurality of apertures having substantially the same flow area may advantageously simplify manufacturing of the cartridge body.

The first air outlet of the first recess of the cartridge body may comprise one or more apertures having any suitable cross-sectional shape. For example, the cross-sectional shape of each aperture may be circular, elliptical, square or rectangular. In embodiments in which the first air outlet of the first recess of the cartridge body comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the first air inlet of the first recess of the cartridge body may be the same as or different to the dimensions of the one or more apertures forming the first air outlet of the first recess of the cartridge body.

Advantageously, the dimensions of the one or more apertures forming the first air inlet of the first recess of the cartridge body may be substantially the same as the dimensions of the one or more apertures forming the first air outlet of the first recess of the cartridge body. Providing a first air inlet and a first air outlet comprising one or more apertures of substantially the same dimensions may advantageously simplify manufacturing of the cartridge body.

Advantageously, the dimensions of the one or more apertures forming the first air outlet of the first recess of the cartridge body may be greater than the dimensions of the one or more apertures forming the first air inlet of the first recess of the cartridge body. Increasing the dimensions of the apertures forming the first air outlet of the first recess of the cartridge body relative to the dimensions of the apertures forming the first air inlet of the first recess of the cartridge body may advantageously reduce the risk of the first air outlet of the first recess of the cartridge body becoming obstructed by, for example, dust.

Advantageously, the flow area of the second air outlet of the second recess of the cartridge body is between about 0.1 square millimetres and about 5 square millimetres.

In embodiments in which the second air outlet of the second recess of the cartridge body comprises a plurality of apertures, the apertures may have different flow areas so that the total flow area of the second air outlet of the second recess of the cartridge body is divided unequally between the apertures forming the second air outlet.

In embodiments in which the second air outlet of the second recess of the cartridge body comprises a plurality of apertures, each of the apertures may have the same flow area so that the total flow area of the second air outlet of the second recess of the cartridge body is divided equally between the apertures forming the second air outlet. Providing a second air outlet comprising a plurality of apertures having substantially the same flow area may advantageously simplify manufacturing of the cartridge body.

The second air outlet of the second recess of the cartridge body may comprise one or more apertures having any suitable cross-sectional shape. For example, the cross-sectional shape of each aperture may be circular, elliptical, square or rectangular. In embodiments in which the second air outlet of the second recess of the cartridge body comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the second air inlet of the second recess of the cartridge body may be the same as or different to the dimensions of the one or more apertures forming the second air outlet of the second recess of the cartridge body.

Advantageously, the dimensions of the one or more apertures forming the second air inlet of the second recess of the cartridge body may be substantially the same as the dimensions of the one or more apertures forming the second air outlet of the second recess of the cartridge body. Providing a second air inlet and a second air outlet comprising one or more apertures of substantially the same dimensions may advantageously simplify manufacturing of the cartridge body.

Advantageously, the dimensions of the one or more apertures forming the second air outlet of the second recess of the cartridge body may be greater than the dimensions of the one or more apertures forming the second air inlet of the second recess of the cartridge body. Increasing the dimensions of the apertures forming the second air outlet of the second recess of the cartridge body relative to the dimensions of the apertures forming the second air inlet of the second recess of the cartridge body may advantageously reduce the risk of the second air outlet of the second recess of the cartridge body becoming obstructed by, for example, dust.

In embodiments in which the cartridge assembly comprises a nicotine source positioned within the first recess and an acid source positioned within the second recess, nicotine vapour released from the nicotine source in the first recess of the cartridge and acid vapour released from the acid source in the second recess of the cartridge may react with one another in the gas phase in the mouthpiece to form an aerosol of nicotine salt particles.

The cartridge assembly may comprise one or more aerosol-modifying agents positioned within the mouthpiece. For example, the mouthpiece may contain one or more sorbents, one or more flavourants, one or more chemesthetic agents or a combination thereof.

The first recess and the second recess may be arranged symmetrically with respect to each other within the cartridge body.

Advantageously, the cartridge is an elongate cartridge. In embodiments in which the cartridge is an elongate cartridge, the first recess and the second recess of the cartridge body may be arranged symmetrically about the longitudinal axis of the cartridge.

The cartridge may have any suitable transverse cross-sectional shape. For example, the transverse cross-sectional shape of the cartridge may be circular, semi-circular, elliptical, triangular, square, rectangular or trapezoidal. Preferably, the transverse cross-sectional shape of the cartridge is square or rectangular.

The cartridge may have any suitable size.

For example, the cartridge may have a length of between about 5 millimetres and about 50 millimetres. Advantageously, the cartridge may have a length between about 10 millimetres and about 20 millimetres.

For example, the cartridge may have a width of between about 4 millimetres and about 10 millimetres and a height of between about 4 millimetres and about 10 millimetres. Advantageously, the cartridge may have a width of between about 6 millimetres and about 8 millimetres and a height of between about 6 millimetres and about 8 millimetres.

The cartridge body, the cartridge cover and the mouthpiece may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The cartridge body, the cartridge cover and the mouthpiece may be formed from the same or different materials.

At least one of the cartridge body and the cartridge cover may be formed from one or more materials that are nicotine-resistant and acid-resistant.

The first recess of the cartridge body may be coated with one or more nicotine-resistant materials and the second recess of the cartridge body may be coated with one or more acid-resistant materials. A first portion of the cartridge cover may be coated with one or more nicotine-resistant materials and a second portion of the cartridge cover may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials may advantageously enhance the shelf life of the cartridge.

Use of one or more acid-resistant materials may advantageously enhance the shelf life of the cartridge.

The cartridge assembly may comprise a heater configured to heat the first recess and the second recess. In such embodiments, the heater is advantageously located between the first recess and the second recess. That is the first recess and the second recess are disposed on either side of the heater.

The heater may be an electrical heater. The heater may be a resistive heater.

Advantageously, the heater is configured to heat the first recess and the second recess of the cartridge body to a temperature of below about 250 degrees Celsius. Preferably, the heater is configured to heat the first recess and the second recess of the cartridge body to a temperature of between about 80 degrees Celsius and about 150 degrees Celsius.

Advantageously, the heater is configured to heat the first recess and the second recess of the cartridge body to substantially the same temperature.

As used herein with reference to the invention, by "substantially the same temperature" it is meant that the difference in temperature between the first recess and the second recess of the cartridge body measured at corresponding locations relative to the heater is less than about 3° C.

The cartridge body may comprise a heater compartment for receiving a heating element of an aerosol-generating device. Preferably, the heater compartment is positioned between the first recess and the second recess. That is, the first recess and the second recess are disposed on either side of the heater compartment. Preferably, the cartridge cover comprises a heater aperture aligned with the heater compartment when the cartridge body is in the second position. Preferably, the heater aperture is provided in the cartridge cover wall portion. In use, a heating element of an aerosol-generating device is received within the heater compartment to heat the first recess and the second recess. The heater aperture may form the actuation aperture. In such embodiments, the heating element of an aerosol-generating device forms an actuator that is received against the cartridge body, through the actuation aperture, to slide the cartridge body from the first position into the second position. Providing a heater aperture that also forms the actuation aperture may simplify the manufacture of the cartridge by reducing the number apertures in the cartridge cover.

The cartridge may comprise a susceptor for inductively heating the first recess and the second recess. In such embodiments, the susceptor is advantageously located between the first recess and the second recess. That is, the first recess and the second recess are disposed on either side of the susceptor.

In use, heating the first recess and the second recess of the cartridge body to a temperature above ambient temperature advantageously enables control of the vapour concentrations of volatile compounds stored within the first and second recesses. For example, in embodiments in which the cartridge assembly comprises a nicotine source positioned within the first recess and an acid source positioned within the second recess, heating the first and second recesses enables the vapour pressure of nicotine in the first recess and the vapour pressure of acid in the second recess to be controlled and balanced proportionally to yield an efficient reaction stoichiometry between the nicotine and the acid. Advantageously, this may improve the efficiency of the formation of nicotine salt particles and the consistency of delivery to a user. Advantageously, it may also reduce the delivery of unreacted nicotine and unreacted acid to a user.

The cartridge body may be formed from one or more thermally conductive materials.

The first recess of the cartridge body and the second recess of the cartridge body may be coated with one or more thermally conductive materials.

Use of one or more thermally conductive materials to one or both of form the cartridge body and coat the interior of the first recess and the second recess of the cartridge body may advantageously increase heat transfer from a heater or a susceptor to the nicotine source and the acid source.

Suitable thermally conductive materials include, but are not limited to, metals such as, for example, aluminium, chromium, copper, gold, iron, nickel and silver, alloys, such as brass and steel and combinations thereof.

The cartridge body may be formed of one or more materials having a low resistivity or a high resistivity depending on whether the first recess and the second recess are heated by conduction or induction.

The first recess of the cartridge body and the second recess of the cartridge body may be coated with one or more materials having a low resistivity or a high resistivity depending on whether the first recess and the second recess are heated by conduction or induction.

The cartridge body may be formed by any suitable method. Suitable methods include, but are not limited to, deep drawing, injection moulding, blistering, blow forming and extrusion.

The cartridge may be designed to be disposed of once the nicotine in the first recess and the acid in the second recess are depleted.

The cartridge may be designed to be refillable.

The mouthpiece may be designed to be disposed of once the nicotine in the first recess and the acid in the second recess are depleted.

The mouthpiece may be designed to be reusable. In embodiments in which the mouthpiece is designed to be reusable, the cartridge is advantageously configured to be removable from the mouthpiece cavity.

The cartridge assembly may simulate the shape and dimensions of a combustible smoking article, such as a cigarette, a cigar, or a cigarillo. Advantageously, in such embodiments the cartridge assembly may simulate the shape and dimensions of a cigarette.

The cartridge assembly may be configured for engagement with the housing of an aerosol-generating device. Preferably, at least one of the cartridge and the mouthpiece is configured for engagement with the housing of an aerosol-generating device.

According to a second aspect of the present invention there is provided a cartridge assembly for use in an aerosol-generating system, the cartridge assembly comprising a cartridge and a mouthpiece. The cartridge comprises a cartridge body and a cartridge cover, the cartridge body having a first side defining a first recess and a second side defining a second recess. The cartridge cover comprises a cartridge cover cavity in which the cartridge body is slidably received and a cartridge cover opening at a downstream end of the cartridge cover cavity. The cartridge cover further comprises a cartridge cover wall portion extending across an upstream end of the cartridge cover cavity and comprising a cartridge cover air inlet, and an actuation aperture in the cartridge cover wall portion for receiving an actuation portion of an aerosol-generating device. The mouthpiece comprises a mouthpiece cavity in which a downstream end of the cartridge is received. The cartridge assembly is configured so that, when an actuation portion of an aerosol-generating device is received against the cartridge body through the actuation aperture, the cartridge body is slidable within the cartridge cover cavity from a first position to a second position. In the first position, an upstream end of the cartridge body abuts the cartridge cover wall portion and obstructs the cartridge cover air inlet, and a downstream end of the cartridge body abuts a downstream end of the cartridge cover and obstructs the cartridge cover opening. In the second position, the upstream end of the cartridge body is spaced apart from the cartridge cover wall portion and the downstream end of the cartridge body is spaced apart from the downstream end of the cartridge cover so that the cartridge cover air inlet is in fluid communication with the cartridge cover opening via the first recess and the second recess. The cartridge assembly according to the second aspect of the present invention may comprise any of the optional or preferred features according to the first aspect of the present invention.

According to a third aspect of the present invention there is provided an aerosol-generating system comprising an aerosol-generating device and a cartridge assembly according to the first aspect of the present invention or the second aspect of the present invention, in accordance with any of the embodiments described herein. The aerosol-generating device comprises a device cavity configured to receive an upstream end of the cartridge assembly, an actuator and a heater. The actuator is positioned within the device cavity and configured to engage the cartridge body through the actuation aperture to slide the cartridge body from the first position into the second position when the cartridge assembly is inserted into the device cavity. The heater is configured for heating the first recess and the second recess of the cartridge of the cartridge assembly when the cartridge assembly is received within the device cavity.

The aerosol-generating device may comprise a device wall extending across an upstream end of the device cavity. The actuator may comprise an actuation pin extending from the device wall portion. The actuation pin is configured so that, when the cartridge assembly is inserted into the device cavity, the actuation pin is received against the cartridge body through the actuation aperture to push the cartridge body from the first position into the second position.

In embodiments in which an inlet aperture forming at least part of the cartridge cover air inlet also forms an actuation aperture, preferably the inlet aperture forming the actuation aperture has a minimum cross-sectional area, wherein, when the cartridge assembly is received within the device cavity and the cartridge body is in the second position, the portion of the actuation pin received within the inlet aperture has a maximum cross-sectional area that is smaller than the minimum cross-sectional area of the inlet aperture. Advantageously, such an arrangement maintains airflow around the actuation pin and through the inlet aperture when the actuation pin is received within the inlet aperture.

In embodiments in which the actuation aperture is a single actuation aperture, the actuation pin is preferably a single actuation pin. In embodiments in which the actuation aperture comprises a plurality of actuation apertures, preferably the actuation pin comprises a plurality of actuation pins each configured for alignment with an actuation aperture when the cartridge assembly is received within the device cavity.

In those embodiments in which the cartridge body comprises a heater compartment for receiving a heating element, the heater of the aerosol-generating device advantageously comprises a heating element positioned within the device cavity and configured to be received within the heater compartment of the cartridge body when the upstream end of the cartridge assembly is received within the device cavity. The heating element may be a resistive heating element. In use, the heating element is received within the third compartment and heats the first recess and the second recess.

The heating element may also be the actuator. That is, when the cartridge assembly is inserted into the device cavity, the heating element is received against the cartridge body, through the actuation aperture, to slide the cartridge body from the first position into the second position. In such embodiments, a heater aperture provided in the cartridge cover also forms the actuation aperture.

In those embodiments in which the cartridge body comprises a susceptor positioned between the first recess and the second recess, the heater of the aerosol-generating device advantageously comprises an inductive heater surrounding at least a portion of the device cavity. In use, the inductive heater inductively heats the susceptor, which heats the first recess and the second recess.

Advantageously, the heater of the aerosol-generating device is configured to heat the first recess and the second recess of the cartridge body to a temperature of below about 250 degrees Celsius. Preferably, the heater of the aerosol-generating device is configured to heat the first recess and the second recess of the cartridge body to a temperature of between about 80 degrees Celsius and about 150 degrees Celsius.

Advantageously, the heater of the aerosol-generating device is configured to heat the first recess and the second recess of the cartridge body to substantially the same temperature.

The aerosol-generating device may further comprise a power supply for supplying power to the heater and a controller configured to control a supply of power from the power supply to the heater.

The aerosol-generating device may comprise one or more temperature sensors configured to sense the temperature of at least one of the heater, the first recess, and the second recess. In such embodiments, the controller may be configured to control a supply of power to the heater based on a sensed temperature.

For the avoidance of doubt, features described above in relation to one aspect of the invention may also be applicable to other aspects of the invention. In particular, features described above in relation to the cartridge assembly of the invention may also relate, where appropriate, to the aerosol-generating systems of the invention, and vice versa.

Embodiments of the invention will now be described, by way of example only, with reference to the accompanying drawings, in which.

Figure 1:
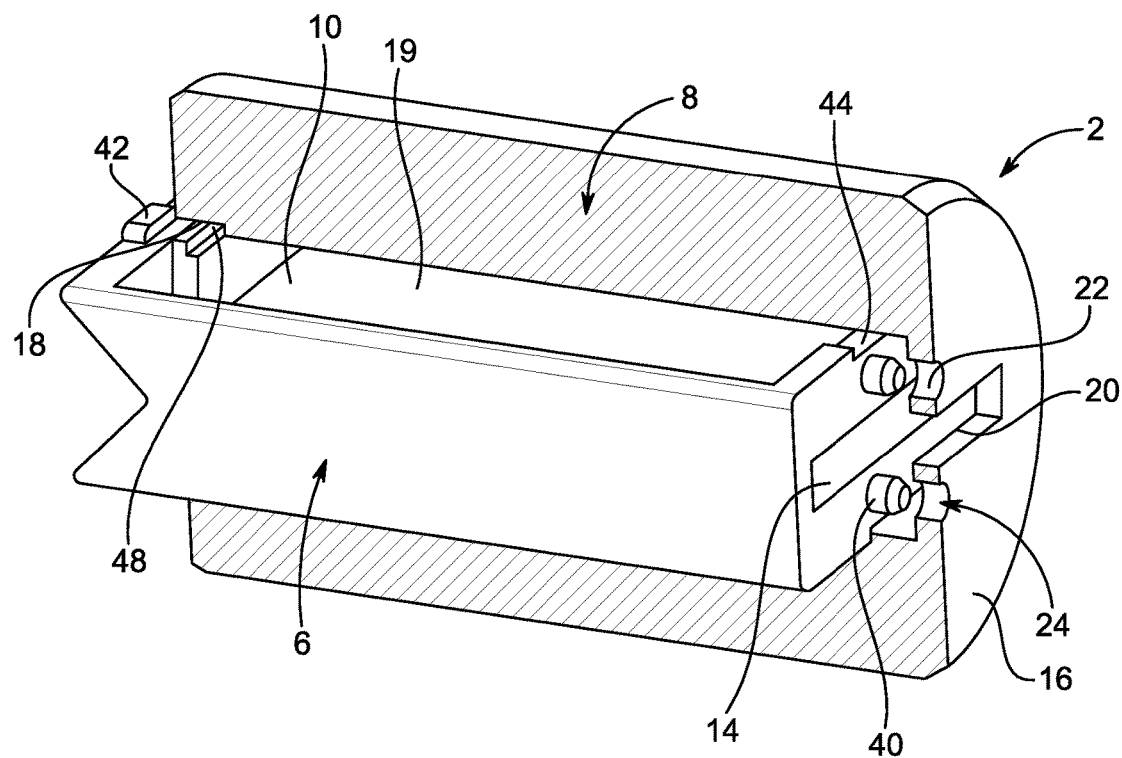
FIG. 1 shows a partial cut-away view of a cartridge in accordance with an embodiment of the present invention.
Figure 2:
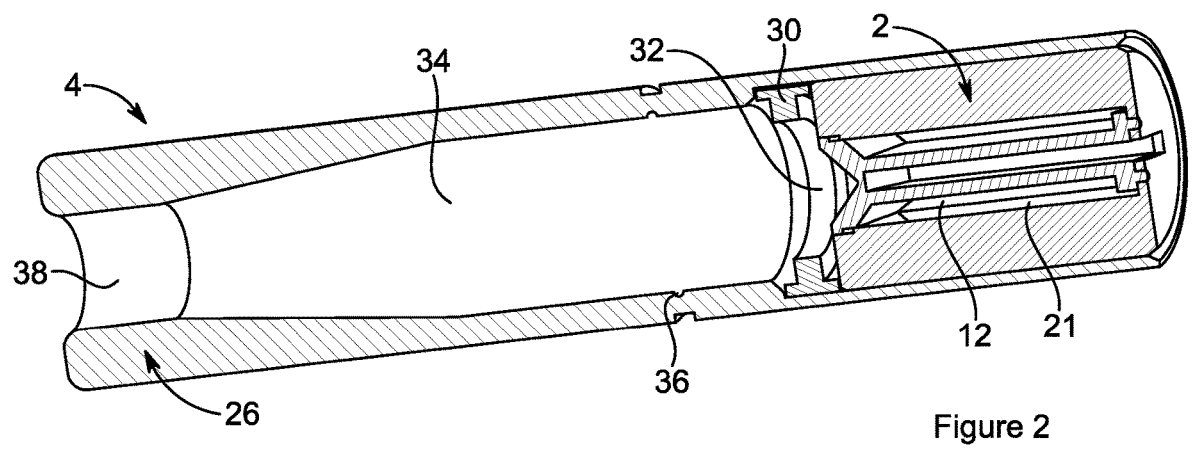
FIG. 2 shows a cross-sectional view of a cartridge assembly comprising the cartridge of FIG. 1, the cartridge assembly in a first configuration.
Figure 3:
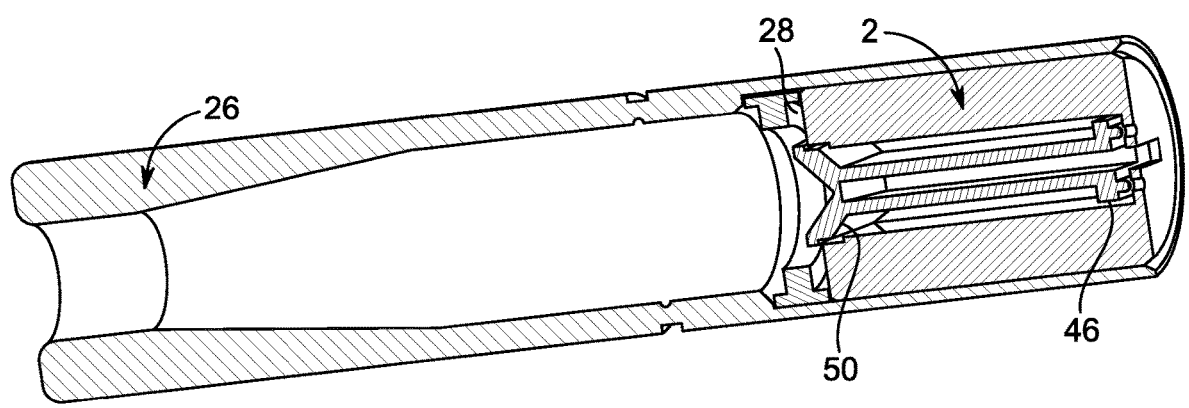
FIG. 3 shows the cartridge assembly of FIG. 2 in a second configuration.

FIG. 1 shows a cartridge 2 in accordance with an embodiment of the present invention. FIGS. 2 and 3 show a cartridge assembly 4 comprising the cartridge 2 of FIG. 1.

The cartridge 2 comprises a cartridge body 6 and a cartridge cover 8. The cartridge body 6 comprises a first recess 10 in which a nicotine source is positioned, a second recess 12 in which an acid source is positioned, and a heater compartment 14 positioned between the first and second recesses 10, 12. The heater compartment 14 may be configured to receive a heating element of an aerosol-generating device. Alternatively, a susceptor may be housed in the heater compartment 14 for heating the first and second recesses 10, 12 via inductive heating of the susceptor using an inductive heater of an aerosol-generating device.

The cartridge cover 8 comprises a cartridge cover wall portion 16 at an upstream end of the cartridge cover 8 and a cartridge cover opening 18 at a downstream end of the cartridge cover 8. A cartridge cover cavity extends between the cartridge cover wall portion 16 and the cartridge cover opening 18, the cartridge body 6 slidably received within the cartridge cover cavity. When the cartridge body 6 is received within the cartridge cover cavity the first recess 10 and the overlying portion of the cartridge cover 8 form a first compartment 19 in which the nicotine source is positioned. When the cartridge body 6 is received within the cartridge cover cavity the second recess 12 and the overlying portion of the cartridge cover 8 form a second compartment 21 in which the acid source is positioned.

The cartridge cover 8 further comprises a heater aperture 20 in the cartridge cover wall portion 16 and aligned with the heater cavity 14. In embodiments in which the heater compartment 14 is configured to receive a heating element of an aerosol-generating device, the heater element is received within the heater compartment 14 through the heater aperture 20.

The cartridge cover 8 also comprises a pair of apertures 22 in the cartridge cover wall portion 16, the pair of apertures forming a combined cartridge cover air inlet and actuation aperture 24.

FIGS. 2 and 3 show a cartridge assembly 4 comprising the cartridge 2 combined with a mouthpiece 26. The mouthpiece 26 comprises a mouthpiece cavity 28 at its upstream end, the cartridge 2 received within the mouthpiece cavity 28. A mouthpiece wall portion 30 is positioned at a downstream end of the mouthpiece cavity 28, the mouthpiece 26 further comprising a mouthpiece air inlet 32 in the mouthpiece wall portion 30.

A mouthpiece chamber 34 is positioned downstream of the mouthpiece wall portion 30, the mouthpiece 26 comprising a ventilation air inlet 36 and a mouthpiece air outlet 38 in fluid communication with the mouthpiece chamber 34.

As shown in FIG. 2, the cartridge body 6 is in a first position with respect to the cartridge cover 8. When the cartridge cover 6 is in the first position, upstream portions 40 of the cartridge body 6 abut the cartridge cover 8 and obstruct the apertures 22 forming the combined cartridge cover air inlet and actuation aperture 24. Additionally, when the cartridge body 6 is in the first position, a downstream portion 42 of the cartridge body 6 abuts the cartridge cover 8 and obstructs the cartridge cover opening 18. Therefore, when the cartridge body 6 is in the first position, airflow through the first and second recesses 10, 12 is substantially prevented, which substantially prevents the loss of nicotine vapour and acid vapour from the first and second compartments 19, 21 respectively.

When the cartridge assembly 4 is combined with an aerosol-generating device to form an aerosol-generating system, an actuator comprising a pair of actuation pins on the aerosol-generating device is received within the apertures 22 of the combined cartridge cover air inlet and actuation aperture 24. The actuation pins push against the cartridge body 6 to slide the cartridge body 6 with respect to the cartridge cover 8 and into a second position shown in FIGS. 1 and 3. The portion of each actuation pin received within each aperture 22 of the combined cartridge cover air inlet and actuation aperture 24 has a diameter that is smaller than the diameter of the respective aperture 22 so that each actuation pin does not entirely obstruct the respective aperture 22.

When the cartridge cover 6 is in the second position, the upstream portions 40 of the cartridge body 6 are spaced apart from the cartridge cover 8 so that air may flow around the actuation pins and through the apertures 22 forming the combined cartridge cover air inlet and actuation aperture 24. Additionally, when the cartridge body 6 is in the second position, the downstream portion 42 of the cartridge body 6 is spaced apart from the cartridge cover 8 so that air may flow through the cartridge cover opening 18. When the cartridge body 6 is in the second position, gaps between the cartridge body 6 and the cartridge cover 8 form a first air inlet 44 at an upstream end of the first compartment 19, a second air inlet 46 at an upstream end of the second compartment 21, a first air outlet 48 at a downstream end of the first compartment 19, and a second air outlet 50 at a downstream end of the second compartment 21. Therefore, when the cartridge body 6 is in the second position, airflow paths are created through the cartridge assembly 4 from the combined cartridge cover air inlet and actuation aperture 24, through the first and second compartments 19, 21 via the first and second air inlets 44, 46 and the first and second air outlets 48, 50, through the mouthpiece air inlet 32, the mouthpiece chamber 34 and the mouthpiece air outlet 38. Ventilation air is also drawn into the mouthpiece chamber 34 through the ventilation air inlet 36 and out of the mouthpiece chamber 34 though the mouthpiece air outlet 38.

In use, when the cartridge assembly 4 is activated, as shown in FIG. 3, nicotine vapour is drawn into the mouthpiece chamber 34 from the first compartment 19 of the cartridge 2 and acid vapour is drawn into the mouthpiece chamber 34 from the second compartment 21 of the cartridge 2. The nicotine vapour and the acid vapour react in the gas phase in the mouthpiece chamber 34 to create an aerosol of nicotine salt particles for delivery to the user through the mouthpiece air outlet 38.

The invention claimed is:

1. A cartridge assembly for an aerosol-generating system, the cartridge assembly comprising:
    a cartridge comprising:
        a cartridge body having a first side defining a first recess and a second side defining a second recess, and
        a cartridge cover comprising:
            a cartridge cover cavity in which the cartridge body is slidably received,
            a cartridge cover opening at a downstream end of the cartridge cover cavity,
            a cartridge cover wall portion extending across an upstream end of the cartridge cover cavity and comprising a cartridge cover air inlet, and
            an actuation aperture in the cartridge cover wall portion configured to receive an actuation portion of an aerosol-generating device; and
    a mouthpiece comprising a mouthpiece cavity in which a downstream end of the cartridge is received,
    wherein the cartridge is configured so that, when an actuation portion of the aerosol-generating device is received against the cartridge body through the actuation aperture, the cartridge body slides within the cartridge cover cavity from a first position to a second position,
    wherein, in the first position, an upstream end of the cartridge body abuts the cartridge cover wall portion and obstructs the cartridge cover air inlet, and a downstream end of the cartridge body abuts a downstream end of the cartridge cover and obstructs the cartridge cover opening, and
    wherein, in the second position, the upstream end of the cartridge body is spaced apart from the cartridge cover wall portion and the downstream end of the cartridge body is spaced apart from the downstream end of the cartridge cover so that the cartridge cover air inlet is in fluid communication with the cartridge cover opening via the first recess and the second recess.

2. The cartridge assembly according to claim 1, wherein an inlet aperture forming at least part of the cartridge cover air inlet forms the actuation aperture.

3. The cartridge assembly according to claim 1,
    wherein the mouthpiece comprises a mouthpiece wall portion extending across the downstream end of the mouthpiece cavity, and
    wherein a downstream end of the cartridge body abuts the mouthpiece wall portion when the cartridge body is in the second position.

4. The cartridge assembly according to claim 1,
    wherein the mouthpiece comprises a mouthpiece chamber position downstream of the cartridge, and wherein the mouthpiece further comprises a mouthpiece air outlet at a downstream end of the mouthpiece chamber.

5. The cartridge assembly according to claim 4, wherein the mouthpiece further comprises a ventilation air inlet providing fluid communication between the exterior of the mouthpiece and the mouthpiece chamber, and wherein the ventilation air inlet is positioned between the cartridge and the downstream end of the mouthpiece chamber.

6. The cartridge assembly according to claim 1, wherein the cartridge further comprises a nicotine source positioned within the first recess and an acid source positioned within the second recess.

7. The cartridge assembly according to claim 1, wherein the cartridge body further comprises a heater compartment configured to receive a heating element of an aerosol-generating device, the heater compartment positioned between the first recess and the second recess, and wherein the cartridge cover comprises a heater aperture aligned with the heater compartment.

8. The cartridge assembly according to claim 7, wherein the heater aperture forms the actuation aperture.

9. The cartridge assembly according to any of claim 1, wherein the cartridge body comprises a susceptor positioned between the first recess and the second recess.

10. An aerosol-generating system, comprising:
a cartridge assembly according to claim 1; and
an aerosol-generating device comprising:
    a device cavity configured to receive an upstream end of the cartridge assembly,
    an actuator positioned within the device cavity and configured to engage the cartridge body through the actuation aperture to slide the cartridge body from the first position into the second position when the cartridge assembly is inserted into the device cavity, and
    a heater configured to heat the first recess and the second recess of the cartridge of the cartridge assembly when the cartridge assembly is received within the device cavity.

11. The aerosol-generating system according to claim 10, wherein the aerosol-generating device comprises a device wall portion extending across an upstream end of the device cavity, and wherein the actuator comprises an actuation pin extending from the device wall portion.

12. The aerosol-generating system according to claim 11, wherein an inlet aperture forming at least part of the cartridge cover air inlet forms the actuation aperture, wherein the inlet aperture has a minimum cross-sectional area, and wherein, when the cartridge assembly is received within the device cavity and the cartridge body is in the second position, the portion of the actuation pin received within the inlet aperture has a maximum cross-sectional area that is smaller than the minimum cross-sectional area of the inlet aperture.

13. The aerosol-generating system according to claim 10, wherein the heater comprises a heating element positioned within the device cavity, wherein the cartridge body further comprises a heater compartment configured to receive the heating element and positioned between the first recess and the second recess, and wherein the cartridge cover comprises a heater aperture aligned with the heater compartment.

14. The aerosol-generating system according to claim 10, wherein the heater comprises a heating element positioned within the device cavity, wherein the cartridge body further comprises a heater compartment configured to receive the heating element and positioned between the first recess and the second recess, wherein the cartridge cover comprises a heater aperture aligned with the heater compartment, wherein the heater aperture forms the actuation aperture, and wherein the heating element is the actuator.

15. The aerosol-generating system according to claim 10, wherein the heater comprises an inductive heater surrounding at least a portion of the device cavity, and wherein the cartridge body comprises a susceptor positioned between the first recess and the second recess.

* * * * *